United States Patent [19]

Karwowski et al.

[11] Patent Number: 4,834,988
[45] Date of Patent: May 30, 1989

[54] METHOD FOR PREPARING A CEREAL

[75] Inventors: Jan Karwowski, Franklin Lakes; Anna M. Magliacano, East Orange; James B. Taylor, Sparta, all of N.J.

[73] Assignee: Nabisco Brands, Inc., Parsippany, N.J.

[21] Appl. No.: 101,489

[22] Filed: Sep. 28, 1987

[51] Int. Cl.$^4$ .............................................. A23L 1/105
[52] U.S. Cl. ........................................ 426/20; 426/28; 426/285; 426/621; 426/625
[58] Field of Search ..................... 426/31, 28, 20, 622, 426/18, 21, 27, 49, 285, 621, 625, 620, 619, 560, 462, 463, 44, 52, 243, 241; 435/99, 96, 94

[56] References Cited

U.S. PATENT DOCUMENTS

| | | |
|---|---|---|
| 651,776 | 6/1900 | Bourdeau .............................. 426/621 |
| 976,332 | 11/1910 | Anhaltzer . |
| 1,108,555 | 8/1914 | Demeny ................................ 426/28 |
| 1,172,270 | 2/1916 | Franzie . |
| 1,178,039 | 4/1916 | Wahl . |
| 1,541,263 | 6/1925 | Hoffman et al. . |
| 1,564,181 | 12/1925 | Kellogg . |
| 1,568,162 | 1/1926 | Humphrey . |
| 2,040,943 | 5/1936 | Kang . |
| 2,174,982 | 10/1939 | Kellogg . |
| 2,206,619 | 8/1939 | Schreier .............................. 426/621 |
| 2,289,416 | 7/1942 | Fine . |
| 2,310,028 | 2/1943 | Gustavson . |
| 2,555,235 | 5/1951 | Huzenlaud . |
| 2,627,464 | 2/1953 | Keahetian . |
| 2,853,388 | 9/1958 | Kiely . |
| 3,157,513 | 11/1964 | Allen et al. . |
| 3,243,301 | 3/1966 | Hesseltine et al. . |
| 3,255,015 | 6/1966 | Blanchon . |
| 3,262,783 | 7/1966 | Blanchon .............................. 426/28 |
| 3,395,019 | 7/1968 | Kviesitis . |
| 3,664,848 | 5/1972 | Bedenk et al. . |
| 3,930,027 | 12/1975 | Kelly et al. . |
| 3,950,543 | 4/1976 | Buffa et al. . |
| 3,956,506 | 5/1976 | Cloud ................................... 426/28 |
| 3,958,015 | 5/1976 | Gay . |
| 3,998,978 | 12/1976 | Lawrence et al. ................... 426/285 |
| 4,038,427 | 7/1977 | Martin ................................. 426/285 |
| 4,056,637 | 11/1977 | Hagiwara et al. . |
| 4,069,103 | 1/1978 | Muller . |
| 4,089,745 | 5/1978 | Antrim et al. . |
| 4,247,636 | 1/1981 | Schoenrock et al. . |
| 4,254,150 | 3/1981 | Fritze et al. . |
| 4,282,319 | 8/1981 | Conrad . |
| 4,292,331 | 9/1981 | Ostre . |
| 4,299,847 | 11/1981 | Morris ................................. 426/18 |
| 4,311,714 | 1/1982 | Goering et al. . |
| 4,371,551 | 2/1983 | Fulger ................................. 426/620 |
| 4,371,551 | 2/1983 | Fulger et al. . |
| 4,374,860 | 2/1983 | Gasser et al. . |
| 4,377,602 | 3/1983 | Conrad . |
| 4,378,432 | 3/1983 | Castelli et al. . |
| 4,379,171 | 4/1983 | Furda .................................. 426/13 |
| 4,431,674 | 2/1984 | Fulger et al. . |
| 4,435,430 | 3/1984 | Fulger et al. . |
| 4,438,150 | 3/1984 | Gantwerker . |
| 4,458,017 | 7/1984 | Horwath et al. . |
| 4,501,814 | 2/1985 | Schoenrock et al. . |
| 4,596,776 | 6/1986 | Nonaka ................................ 435/96 |
| 4,613,507 | 9/1986 | Fulger ................................. 426/619 |
| 4,656,040 | 4/1987 | Fulger et al. ....................... 426/18 |
| 4,663,168 | 5/1987 | Von Fulger .......................... 426/28 |

FOREIGN PATENT DOCUMENTS

| | | |
|---|---|---|
| 78782 | 11/1983 | European Pat. Off. . |
| 37-1654 | 5/1962 | Japan . |
| 53-62848 | 6/1978 | Japan . |
| 57-47465 | 3/1982 | Japan . |
| 622028 | 3/1981 | Switzerland . |

OTHER PUBLICATIONS

Reed 1966 Enzymes in Food Processing, Academic Press, New York, pp. 46, 47, 52, 53, 61–67 and 269–271.

*Primary Examiner*—Donald E. Czaja
*Assistant Examiner*—Carolyn Paden
*Attorney, Agent, or Firm*—Richard Kornutik

[57] ABSTRACT

A hot cereal is prepared by treating a cereal grain with a slurry resulting from the treatment of a grain-water mixture with starch-converting enzymes, heating the mixture until the grain is at least partially cooked, flaking the cooked cereal, and, optionally, agglomerating the flakes. It is preferred that the flakes be agglomerated for packaging in single-sized point of sale containers. This cereal has a rich, nutty flavor and when prepared does not have a gummy texture.

29 Claims, No Drawings

METHOD FOR PREPARING A CEREAL

BACKGROUND OF THE INVENTION

This invention relates to a method for preparing a high grain content hot cereal. More particularly, this invention relates to a method for quickly and conveniently preparing a hot high grain content cereal.

It is the objective of the present invention to prepare a natural hot cereal having a high grain content. The hot cereal will consist primarily of natural grains. It is considered to be very time-consuming to prepare hot cereals. Also, hot cereal, when cooked at home, usually is prepared in more than a single-serving size. Therefore, for the reason that in the usual case of home preparation the preparation of a hot cereal is time-consuming, the popularity of hot cereals for breakfast has decreased. In contrast, cold cereals can be quickly prepared and consumed. Cold cereals can also be easily and readily prepared in single-serving sizes. Consequently, cold cereals have become much more popular. It is the intention here to describe a method which can be used to prepare single-sized servings of hot cereal quickly and easily.

The hot cereal compositions that are to be prepared consist primarily of natural grains. Some sugar can be added for the purpose of forming cereal agglomerates. In addition, flavorants and other materials can be present. The cereal is packaged in single-serving sized containers for the convenience of the consumer. The consumer, in order to prepare one of the cereals, opens the container, adds a liquid such as milk or water, and then heats the cereal in an oven, which is preferably a microwave oven. The cereal is quickly heated and rehydrated. The cereal is then ready for consumption.

The present cereal is preferably packaged in a container which can be inserted into a microwave oven. The cereal can be consumed from the same container. The objective is to provide sufficient convenience to induce the consumer to add hot cereals to his diet.

The present hot cereal composition is essentially a precooked cereal which, after cooking, is dried, formed into flakes and, optionally, agglomerated. The cereal can be prepared for eating in either an unagglomerated or agglomerated form. However, when the cereal is to be packaged and to undergo storage and handling, it is preferred that the cereal be in the form of agglomerates. The reason is that during handling the flakes will break down to smaller particles and to a powder. On the other hand, the agglomerates can withstand handling and when the package is opened there are visually particles of a cereal which are similar in shape and size to the original grains.

The cereal is colored, flavored and texturized through the use of an enzyme-treated grain. Any grain can be used. These include wheat, oats, corn, rye, rice, barley and mixtures of these grains. Grain flours can also be used. Enzymes are selected that will hydrolyze the starch of the grain and produce dextrins, glucose and fructose. The enzyme treatment, in conjunction with thermal processing steps, will also produce solids that have a nutty flavor. This will enhance the flavor of the grain that is to be the major component of the cereal. The treatment will also enhance the texture of the cereal.

A process for preparing an all grain enzyme-saccharified cereal is described in U.S. Pat. No. 4,656,040. This process involves saccharifying an endosperm fraction to form a syrup containing soluble saccharides and adding to the saccharified endosperm a minor amount of a matrix-forming ingredient which is a modified bran material or a toasted ground germ. This results in the formation of a cereal dough which is converted to flakes. The flakes contain about 15 percent by weight of the matrix grain with the remainder being saccharified endosperm (optionally some unsaccharified endosperm) and water. This is a minor amount of matrix grain. However, if a large amount of matrix grain were used, a cereal dough, which is an objective of the invention, would not be formed.

SUMMARY OF THE INVENTION

In the present process for preparing a hot cereal, a mixture of water and a grain is formed. This mixture can be heated and one or more starch-converting enzymes then added or the grains, water and starch-converting enzymes combined and heated at a temperature of about 50° C. to 100° C., and preferably about 60° C. to 80° C. If a plurality of enzymes are added, these can be added together or sequentially. Enzyme treatment is continued until about 20 percent by weight, and preferably about 70 to 80 percent by weight of the starch of the grains has been hydrolyzed and converted to monosaccharides, and in particular converted to fructose. The enzymes work on the grains to form an enzyme processed slurry of dextrins, fructose, glucose and other components that will be used in the subsequent step of cooking the primary grain that will comprise the cereal. In the preferred process, three different enzymes are used. These are added sequentially. The objective is to produce an enzyme processed slurry containing fructose, flavorants which will yield a nutty flavor and texture enhancing materials. In a second step, a minor amount of this slurry is added to a mixture of raw grains and water. This mixture is heated for from about 7 minutes to about 60 minutes and preferably about 10 to 50 minutes at a cooking temperature of about 100° C. to 150° C., and preferably about 110° C. to 140° C. This cooking can be conducted from atmospheric to an elevated pressure. After the cooking is completed, the cooked grains are dried and converted into flakes. The flakes can then be used directly or can be formed into agglomerates. Essentially, any process for forming agglomerates from flaked material can be used. Agglomerates can be formed using milk solids, corn syrup solids and other substances. However, one preferred process is that of U.S application Ser. No. 54,492 filed May 27, 1987. This process consists essentially of adding sugar to the cereal grains or flakes and heating the mixture. Flavorants can also be added along with the sugar. The result is agglomerates which can withstand the handling that would be experienced during shipping. When used by the consumer, all that is necessary is that milk or water be added and the mixture be heated in an oven, preferably in a microwave oven. In a preferred embodiment, the cereal would be sold to the consumer in single-serving sized containers such as those which are described in U.S. patent application Ser. No. 54,493 filed May 27, 1987. Dried fruits can also be an part of the cereal in the container or can be an integral part of the cereal in the container or can be in a separate compartment and added by the consumer.

DETAILED DESCRIPTION OF THE INVENTION

An objective is to produce a precooked hot cereal which is naturally colored, flavored and texturized. This is accomplished by adding to a cereal grain to be cooked a minor amount of an enzyme processed slurry, derived from one or more grains. This enzyme processed slurry also contains glucose, fructose and dextrins and when added to a cereal grain the cereal grain is sweetened to a degree by this slurry. The degree of sweetening depends on the amount of slurry added. Fructose has a high sweetening power so the slurry will have a greater sweetening effect on the cereal grain than would the use of sugar at the same level. The flavor will also be enhanced, with the cereal having a rich nutty taste and an enhanced texture.

As a first step, a mixture is formed containing one or more of the enzymes, one or more grains and water. Essentially any grain can be used. Those that can be used include wheat, oats, rye, rice, corn, barley and mixtures of these grains. Grain flours can also be used. Stabilizers and pH buffers can also be added. At least one of the starch-converting enzymes is then added. The preferred starch-converting enzymes are alpha amylase, glucoamylase and glucose isomerase. Pullulanase can also be used. Pullulanase hydrolyzes branches on the starch chains and can be used in conjunction with, or in place of alpha amylase. These can be added separately, together or in any combination. Pullulanase would usually be added in combination with the alpha amylase when both alpha amylase and pullulanase are to be used. A main objective is to hydrolyze the starch in the grain. It is also an objective to produce fructose. For instance, the glucose isomerase will convert some of the dextrose that is initially produced to fructose. The ratio of grain to total enzyme used on a dry basis will be about 10:1 to about 200:1 by weight, and preferably about 20:1 to about 100:1. It is preferred that the enzymes not be added together. The preferred sequence is that the alpha amylase, and optionally pullulanase, be added first, followed by the addition of glucoamylase, and then by the addition of the glucose isomerase. The water-grain-enzyme mixture is preferably heated subsequent to the addition of each enzyme. However, the alpha amylase and glucoamylase can be added together. This can also contain pullulanase. In that case the glucose isomerase is then added after the addition of the alpha amylase and glucoamylase and the partial hydrolysis of the starch. Additionally the glucoamylase and glucose isomerase can be added together after treatment with alpha amylase, optionally also containing pullulanase. Regardless of the mode of addition, the resulting enzyme slurry will contain about 10 percent to 30 percent by weight of fructose and about the same percent by weight of dextrose on a dry basis. The remainder will be the flavor and texture enhancing components and some non-hydrolyzed starch.

Regardless of the mode or sequence of the addition of the enzymes, the enzyme-grain slurry is preferably heated until about 20 percent by weight, and preferably about 75 percent by weight, of the starch has been hydrolyzed. During this period of time the enzymes act on the grain to produce a grain substantially depleted of starch.

The preferred mode of addition is to first add the alpha amylase. Pullulanase can be added along with the alpha amylase. The mixture of water, grain and alpha amylase is maintained at above about 60° C., and preferably above about 90° C. However if pullulanase is present the temperature is maintained at less than about 80° C. This is continued until the starch is partially gelatinized. The glucoamylase is then added and the temperature maintained at about 20° C. to 80° C., and preferably about 55° C. to 75° C. This is continued until at least about 20 percent, and preferably 75 percent of the starch content of the grain has been hydrolyzed. The glucose isomerase is then added. Although the temperature can range from about 20° C. to 100° C. during treatment with glucose isomerase, it is preferred that the temperature be maintained at about 60° C. to 80° C. Treatment with glucose isomerase is continued until the fructose content is at least about 20 percent by weight (dry basis), and preferably at least about 50 percent by weight, of the monosaccharide content of the resulting enzyme processed slurry.

It is also feasible to add the glucoamylase and glucose isomerase together after the grain-water mixture has been treated with the alpha amylase, and optionally with pullulanase. In such a case, the temperature should be maintained at about 20° C. to 80° C., and preferably about 55° C. to 75° C. Likewise this treatment will be continued until the fructose content of the slurry is at least about 20 percent by weight (dry basis), and preferably at least about 50 percent by weight, of the monosaccharide content of the resulting enzyme processed slurry.

Another mode of addition is to first treat the grain-water mixture with the combination of alpha amylase and glucoamylase followed by treatment with glucose isomerase. The mixture can also contain pullulanase. When the alpha amylase and glucoamylase are added together the temperature is maintained at about 20° C. to 100° C. and preferably about 40° C. to 80° C. After there has been substantial starch hydrolysis, the glucose isomerase is added and the temperature maintained in the same range. Treatment with glucose isomerase is continued until the fructose content is at least about 20 percent by weight (dry basis), and preferably about 50 percent by weight, of the monosaccharide content of the resulting enzyme processed slurry.

A further mode of addition is to add all of the enzymes to the grain-water mixture at the same time. In this embodiment the temperature is maintained at about 20° C. to 100° C., preferably about 50° C. to 95° C., and most preferably about 60° C. to 80° C. for a period of time to hydrolyze at least about 20 percent by weight of the starch content of the grain, and preferably about 75 percent by weight of the starch content. This period of time should also be sufficient to yield a fructose content that is at least about 20 percent by weight (dry basis), and preferably at least about 50 percent by weight, of the monosaccharide content of the resulting enzyme processed slurry.

In the present processes suitable enzyme concentrations relative to grain are from 1 Liq./g to about 1000 Liq./g for alpha amylase, from about 0.1 GU/g to about 10 GU/g for glucoamylase and from about 1 IGIU/g to about 100 IGIU/g for glucose isomerase. The exact amount of enzymes chosen for any run depends on the particular grain and the desired processing time. As used in this paragraph g means grams on a dry basis. IGIU is an abbreviation for International Glucose Isomerase Unit and is the amount of enzyme that will convert 1 micromole of glucose to fructose in a designated solution containing 2 moles of glucose per liter. GU is the glucoamylase unit and is defined as the amount of enzyme which catalyzes the production of one gram of dextrose per hour at 60° C. and a pH of 4.5. Liq. is an abbreviation for liquefons which is an enzyme activity defined by Standard Test Method AATCC 103-1965 as published in the 1967 Edition of Technical Manual of the American Association of Textile Chemists and Colorists. Pullulanase, when used to replace alpha amylase, would be added in an amount of about 50 to 150 percent by weight of the alpha amylase that would be used. When used in conjunction with alpha amylase it is added in an amount of about 10 to about 90 percent by weight of the alpha amylase content.

The pH of the grain-water-enzyme slurry should be maintained at about 5 to 9, and preferably about 5 to 8, during hydrolysis of the starch. When the enzymes are added together, the pH should be maintained in this range throughout treatment. When the enzymes are added separately the pH during alpha amylase treatment should preferably be about 5 to 8. During the treatment with glucoamylase, the pH should preferably be about 4 to 6, and during the treatment with glucose isomerase preferably in the range of about 5 to 9. If, after treatment with alpha amylase, the grain-water mixture is treated with a combination of glucoamylase and glucose isomerase, pH should be maintained within the range of about 5 to 8. When the grain is treated with a combination of alpha amylase and glucoamylase the pH is preferably maintained at about 5 to 8. During the subsequent treatment with glucose isomerase the pH would be maintained in the range of about 5 to 9. When pullulanase is present, the pH should preferably not exceed about 7.5.

Essentially, any edible base or acid can be used to adjust the pH. These include calcium carbonate, magnesium hydroxide, sodium hydroxide and potassium hydroxide, propionates, lactates, fumarates, malates, citrates and phosphates. Citric acid can also be used.

A minor amount of this enzyme processed slurry is blended into a mixture of raw grain or grains which may also contain salt. The grains can be any of oats, wheat, rye, barley, rice, corn or mixtures of these grains. The enzyme processed slurry is present in a weight ratio of about 1 percent by weight to about 45 percent by weight of the grain. The water content of the grain-enzyme processed slurry mixture should be about 10 percent to 25 percent by weight, and preferably about 15 to 20 percent. This mixture is heated for a period of time of about 7 to about 60 minutes at a temperature of about 100° C. to 150° C., and preferably about 110° C. to 140° C. Heating can be conducted at atmospheric pressure up to a pressure of about 25 psig, and preferably up to about 20 psig. After heating, the cereal can be dried and flaked or flaked and dried. When dried the grain mixture is dried to a moisture content of about 8 percent to 20 percent by weight, and preferably about 10 to 16 percent by weight. Drying can be accomplished using any type of conventional dryer. A suitable apparatus for converting the cereal to flakes is a flaking mill. The cereal, in the form of flakes, may be directly used by the consumer or, in the alternative, the flakes and other ingredients can be converted to agglomerates which are then used by the consumer. Any agglomeration process can be used. In any regards, whether the cereal is in a flake or agglomerate form, all that is necessary is that water or milk be added and the mixture heated in a microwave or a convection oven. It is preferred that a microwave oven be used. Flavorants and fruits can be added to the cereal before or after heating.

In the preferred process for forming the agglomerates, the flakes should have a moisture content of about 10 to 18 percent by weight. Sugar is added in an amount of about 10 to 45 percent by weight, and preferably 20 to 35 percent by weight, of the cereal composition. Flavorants can also be added. Suitable flavorants comprise vanilla, cinnamon, nutmeg, a nut product or a fruit product such as dried fruits, or mixtures thereof. Essentially any fruit flavorant can be used, with the most common being apple, peach, pear, apricot, blueberry, strawberry, pineapple or raisin. The grain flakes, sugar and flavorants are mixed together using a mechanical action or tumbling, and then heated to a temperature where the sugar liquifies. This is typically to a temperature of about 90° C. to 100° C. Microwave energy is the preferred mode of heating. Upon cooling, the sugar resolidifies and bonds the flakes and flavorants into agglomerates. Dried fruits would be added to the agglomerates prior to the final packaging.

The cereal is preferably packaged in single serving containers. In such a packaging, a consumer need only open the container, add water or milk, and heat the container, preferably in a microwave oven. The cereal is heated and rehydrated within about 1 to 2 minutes. It can then be consumed directly from the container.

The treatment of the raw grains with the enzyme processed slurry enhances the color, flavor and texture of the cooked cereal. Such a treated cereal has a richer nutty flavor and, from a texture point of view, the cereal is less gummy when being consumed. The net result is a cooked cereal that is ready to be consumed which has an improved visual appearance, a wholesome flavor and is appetizing.

The invention will now be described with particular reference to the following examples.

EXAMPLE 1

A wheat and water are mixed in a jacketed heating kettle. This mixture is 58.4 percent by weight wheat and 29 percent by weight water. Alpha amylase is added and the temperature of the mixture increased to 95° C. for about 20 minutes. The temperature is reduced to 65° C and glucoamylase is added. The mixture is then maintained at this temperature for about 30 minutes. Magnesium hydroxide is added to buffer the mixture and glucose isomerase is then added. This mixture is maintained at 70° C. for about 60 minutes. The temperature of the mixture is then reduced to about room temperature and citric acid is added to maintain the pH at about 6.5 to 7. The total enzyme content is 1.84 percent by weight. The ratio in percent by weight of the alpha amylase to glucoamylase to glucose isomerase is about 0.28 to 1.4 to 0.16. The fructose content is approximately 11 percent by weight of the slurry.

EXAMPLE 2

5.63 kilograms of the enzyme slurry of Example 1 is mixed with 4.13 kilograms of water until the water and slurry are well mixed. This slurry mixture is then added into a mixture of 89.24 kilograms of steel-cut oats and 1 kilogram of salt. During slurry addition, the oats are agitated with agitation continuing for about 10 minutes after the addition has ceased. The moisture content of the oat mixture is about 18 percent. This mixture is then heated in a sealed pressure vessel at 120° C. for about 15 minutes. Steam is added during heating. The pressure is 14 psig. The cooked product will have a moisture content of about 20 to 22 percent by weight. The cooked oats are cooled and large pieces are reduced in size. The oat mixture is dried to a moisture content of 12 to 14 percent by weight. The dried material is then passed through a #6 screen and held in a tempering bin to equalize moisture. Oversized pieces are ground and recycled. The oats are then flaked using flaking rolls. The moisture content of the flakes is about 12 to 14 percent by weight.

EXAMPLE 3

A blend of sweetener, flavorants, and other minor components is made at room temperature according to the following formulation:

Sugar—10.2 grams

Flavorants (Cinnamon, salt, non-fat milk solids, malic acid)—1.6 grams

Guar gum—0.2 gram

Diglycerides—0.01 gram

Vitamin and mineral ingredients—0.48 gram

This blend is then mixed with the following grain mixture at room temperature:

Processed wheat—3 grams

Flaked oats—15 grams

Rolled barley—3 grams

After the grains have been added into the combination of sweeteners and flavorants water is sprayed into the mixture at room temperature in an amount of up to about 2 percent by weight of the total mixture. After the addition of the sprayed water, the mixture is blended until homogeneous. The mixture is spread out evenly and then heated in a microwave oven to a temperature of about 100° C. This microwave heating is completed in about 1 minute. The agglomerates that are formed are then allowed to cool and are packaged. Prior to packaging, dried fruit pieces may be blended with the agglomerates by tumbling. Alternatively, the dried fruit may be packaged separately and added by the consumer to the cereal after reconstitution and microwave heating.

What we claim is:

1. A method for preparing a cereal comprising:
   (a) heating an aqueous slurry containing at least one added starch hydrolyzing enzyme, at least one added glucose isomerizing enzyme and at least one grain at a pH and at a temperature at which said at least one starch hydrolyzing enzyme and at least one glucose isomerizing enzyme exhibit significant enzymatic activity and until at least about 20 percent of the starch content of said grain has been hydrolyzed to glucose and at least a portion of said glucose converted to fructose;
   (b) combining at least a portion of said aqueous slurry with at least one cereal grain to form a cereal mixture wherein the weight ratio of said aqueous slurry to said cereal grain is about 1 percent by weight to about 45 percent by weight;
   (c) heating said cereal mixture; and
   (d) forming the cereal mixture into a final shape.

2. A method for preparing a cereal as in claim 1 wherein said cereal shapes are dried to a moisture content of about 8 to 20 percent by weight.

3. A method for preparing a cereal as in claim 1 wherein said cereal mixture is dried to a moisture content of about 8 to 20 percent by weight prior to said cereal mixture being formed into shapes.

4. A method for preparing a cereal as in claim 1 wherein said cereal flakes are agglomerated.

5. A method for preparing a cereal as in claim 4 wherein said cereal shapes are flakes and are agglomerated by mixing sugar with said cereal flakes and the sugar cereal flakes mixture is heated to form cereal agglomerates.

6. A method for preparing a cereal as in claim 5 wherein a liquid is combined with said cereal agglomerates and the combination is heated.

7. A method for preparing a cereal as in claim 6 wherein said heating is microwave heating.

8. A method for preparing a cereal as in claim 6 wherein said heating is convection heating.

9. A method for preparing a cereal as in claim 5 wherein said sugar-cereal flake mixture is heated by convection heating to form agglomerates.

10. A method for preparing a cereal as in claim 5 wherein said sugar-cereal mixture is heated by microwave heating to form agglomerates.

11. A method for preparing a cereal as in claim 1 wherein said cereal grain is selected from the group consisting of oats, wheat, rice, corn, barley, rye and mixtures thereof.

12. A method for preparing a cereal as in claim 1 wherein said grain is selected from the group consisting of oats, wheat, rice, corn, barley, rye, flours thereof, and mixtures of the foregoing.

13. A method for preparing a cereal as in claim 1 wherein said starch-hydrolyzing enzymes are selected from the group consisting of alpha amylase, pullulanase, glucoamylase, and mixtures thereof.

14. A method for preparing a cereal as in claim 4 wherein said starch-hydrolyzing enzymes are selected from the group consisting of alpha amylase, pullulanase, glucoamylase and mixtures thereof.

15. A method for preparing a cereal as in claim 1 wherein water is added to the mixture of said aqueous slurry prior to being added to the cereal grain.

16. A method for preparing a cereal as in claim 14 wherein said cereal mixture is heated at an elevated pressure of up to about 25 psig.

17. A method for preparing a cereal as in claim 12 wherein said grain is treated with alpha amylase, followed by treatment with glucoamylase and then by glucose isomerase.

18. A method for preparing a cereal as in claim 12 wherein said grain is treated with alpha amylase and glucoamylase followed by treatment with glucose isomerase.

19. A method for preparing a cereal as in claim 1 wherein the grain that is mixed with said enzymes is selected from the group consisting of oats and wheat.

20. A method for preparing a cereal comprising:
   (a) heating an aqueous slurry containing at least one added starch hydrolyzing enzyme the addition of glucoamylase and the addition thereof of glucose isomerase and a grain at a pH and at a temperature at which said starch hydrolyzing enzyme, said glucoamylase and said glucose isomerase exhibit significant enzymatic activity until at least about 20 percent of the starch content of said grain has been hydrolyzed to glucose and at least a portion of said glucose converted to fructose;
   (b) combining at least a portion of said aqueous slurry with a cereal grain to form a cereal mixture wherein the weight ratio of said aqueous slurry to said cereal grain is about 1 percent to about 45 percent;
(c) heating said cereal mixture; and
(d) forming the cereal mixture into flakes.

21. A method for preparing a cereal as in claim 20 wherein said cereal flakes are formed into agglomerates.

22. A method for preparing a cereal as in claim 21 wherein in the formation of agglomerates said cereal flakes are combined with sugar and heated.

23. A method for preparing a cereal as in claim 20 wherein said grain is selected from the group consisting of oats, corn, wheat, rye, rice, barley, flours thereof and mixtures of the foregoing.

24. A method for preparing a cereal as in claim 20 wherein said cereal grain is selected from the group consisting of oats, wheat, rice, corn rye, barley and mixtures thereof.

25. A method for preparing a cereal as in claim 20 wherein said cereal mixture is heated at an elevated pressure of up to about 25 psig.

26. A method for preparing a cereal as in claim 21 wherein a liquid is added to said agglomerates and the liquid-agglomerate mixture is heated.

27. A method for preparing a cereal as in claim 20 wherein said liquid-agglomerate mixture is heated by microwave heating.

28. A method for preparing a cereal as in claim 20 wherein alpha amylase is added, followed by the addition of glucoamylase and the subsequent addition of glucose isomerase.

29. A method for preparing a cereal as in claim 20 wherein alpha amylase and glucoamylase are added followed by the addition of glucose isomerase.

* * * * *